(12) United States Patent
Steaffens et al.

(10) Patent No.: US 6,579,688 B2
(45) Date of Patent: Jun. 17, 2003

(54) STABILIZING DILUENT FOR POLYPEPTIDES AND ANTIGENS

(75) Inventors: Jeffrey W. Steaffens, Lafayette, CO (US); Laura Panzarella, Longmont, CO (US)

(73) Assignee: Biostar, Inc., Boulder, CO (US)

( * ) Notice: Subject to any disclaimer, the term of this patent is extended or adjusted under 35 U.S.C. 154(b) by 0 days.

(21) Appl. No.: 09/737,635

(22) Filed: Dec. 14, 2000

(65) Prior Publication Data

US 2002/0076813 A1 Jun. 20, 2002

Related U.S. Application Data

(60) Provisional application No. 60/170,850, filed on Dec. 14, 1999.

(51) Int. Cl.[7] ............................ G01N 33/53; C12Q 1/70; A61K 45/00
(52) U.S. Cl. .................. 435/7.92; 435/7.8; 435/7.1; 435/7.2; 435/7.21; 435/68.1; 435/69.1; 435/69.6; 435/172.1; 435/173.1; 435/252.3; 435/320.1; 435/811; 424/85; 424/133.1; 424/135.1; 424/145.1; 424/810; 536/23.1; 536/23.53; 536/23.72; 530/387.3; 530/388.25; 530/388.73; 530/868; 436/8; 436/16; 436/18; 436/176; 436/548; 436/826
(58) Field of Search ................ 435/7, 7.1, 7.2, 435/7.21, 69.1, 68, 172.11, 172.3, 320.1, 811, 69.6, 252.3, 7.92; 424/85, 33.1, 135.1, 145.1, 810; 536/23.1, 23.72, 23.53; 530/387.3, 388.73, 868, 388.25; 436/548, 8, 16, 18, 176

(56) References Cited

U.S. PATENT DOCUMENTS

| | | | |
|---|---|---|---|
| 4,496,537 A | * | 1/1985 | Kwan ........................ 424/85 |
| 4,956,274 A | | 9/1990 | Khanna et al. |
| 5,316,910 A | * | 5/1994 | Rota et al. ................... 435/7.1 |
| 5,459,033 A | | 10/1995 | Vonwirth et al. |
| 5,541,057 A | | 7/1996 | Bogart et al. |
| 5,550,063 A | | 8/1996 | Bogart |
| 5,660,978 A | | 8/1997 | Kwan et al. |
| 5,955,377 A | | 9/1999 | Maul et al. |
| 5,955,448 A | | 9/1999 | Colaco et al. |
| 5,994,511 A | * | 11/1999 | Lowman et al. ......... 530/387.3 |
| 6,172,213 B1 | * | 1/2001 | Lowman et al. ......... 536/23.53 |

FOREIGN PATENT DOCUMENTS

| | | | |
|---|---|---|---|
| EP | 0524803 | 1/1993 | ........... C07K/13/00 |
| JP | 10191972 | 7/1998 | ........... C12N/9/96 |
| WO | WO 9611018 | 4/1996 | ......... A61K/38/21 |
| WO | WO 97/04801 A1 | 2/1997 | |
| WO | WO 9741209 | 11/1997 | ........... C12N/5/06 |
| WO | WO 9817242 | 4/1998 | ........... A61K/7/42 |
| WO | WO 99/15901 A1 | 4/1999 | |

OTHER PUBLICATIONS

Landi, S. and Held, HR, Tubercie 59 (1978) 121–133.

International Search Report, Mar. 30, 2001.

* cited by examiner

*Primary Examiner*—Long V. Le
*Assistant Examiner*—Lisa Cook
(74) *Attorney, Agent, or Firm*—Foley & Lardner; Richard J. Warburg

(57) ABSTRACT

Compositions for stabilizing polypeptides or antigens are described. These compositions are useful for stabilizing polypeptides or antigens stored in aqueous formulations. Such formulations can be used for various analytical or other methods.

20 Claims, 1 Drawing Sheet

STABILIZING DILUENT FOR POLYPEPTIDES AND ANTIGENS

This application is related to U.S. provisional patent application No. 60/170,850, filed Dec. 14, 1999, entitled "STABILIZING DILUENT FOR POLYPEPTIDES AND ANTIGENS," from which priority is claimed, and which is hereby incorporated by reference in its entirety, including all claims, figures, and tables.

FIELD OF THE INVENTION

The present invention relates to aqueous compositions useful for stabilizing polypeptides and antigens. The stabilized polypeptides and antigens are useful in analytic methods such as antigen-specific detection, as well as other pharmaceutical uses where the stabilization of such components in an aqueous solution is desirable.

BACKGROUND OF THE INVENTION

The following is a discussion of literature potentially relevant to the invention disclosed herein. However, none of the references discussed herein is admitted to be prior art.

Stabilizing polypeptides and antigens in aqueous solutions is often difficult. For example, storage of such solutions at room temperature for prolonged periods results in deterioration of polypeptides or antigens contained in the aqueous solution. In particular, antigens of bacteria, viruses, and other microorganisms have been documented to be unstable when stored in an aqueous medium. One example is enveloped viruses, such as influenza viruses of the Orthomyxovirus family that contain antigens that degrade in solution over time at a broad range of storage temperatures. Those of ordinary skill in the art understand that stabilization in solution of various bacterial antigens, for example, some toxins, is also difficult. To avoid deterioration in an aqueous solution those skilled in the art have used lyophilization and freezing as methods for preserving polypeptides or antigens. Indeed, the widespread use of lyophilization and freezing demonstrates the shortcomings and difficulties of preserving such components in aqueous solutions.

Numerous publications in the art disclose means of increasing the stability of a lyophilized reagent, and the difficulties inherent even within this state of the art technology. For example, U.S. Pat. Nos. 5,955,448, 4,496,537, and PCT filing WO 97/04801 all disclose improvements in lyophilization techniques. Lyophilization of protein containing solutions, however, imposes major costs and inconvenience on the manufacturer and the end user, as well as introducing an increased risk for reconstitution errors and contamination. Additionally, freezing of a solution requires special equipment and ultimately can lead to protein degradation when repeated cycling occurs. For commercial use, deterioration of polypeptides and antigens in aqueous solutions is costly because such solutions require replacement after only a short storage life.

This invention concerns an aqueous stabilizing reagent or diluent that enhances the stability of polypeptides, and other non-proteinaceous compounds in solution. Antigens such as carbohydrates, proteins, lipoproteins, lipopolysaccharides, polysaccharides, nucleic acids, nucleoproteins, and carbohydrates complexed with proteins, lipids, and other compounds are illustrative examples of the types of antigens that may be stabilized using the current invention. Using novel reagent components, the invention improves the stability of polypeptides and antigens in current commercially available diluents or diluents described in the art. The invention is especially useful for stabilizing antigens and polypeptides used as control reagents in diagnostic assays or other uses that require stable aqueous solutions of such components. The stabilizing diluent of the present invention is useful for stabilizing polypeptides and antigens for storage at about 2°–8° C., room temperature and at temperatures of about 45° C. for extended periods of time.

PCT filing No. WO99/15901 discloses a diluent for the stabilization of antigens, in particular, Hepatitis C Virus (HCV) antigens. The HCV diluent comprises a reducing agent to keep the HCV antigens in a reduced form. The publication reports that the inclusion of a reducing agent in a diluent maintained the immunoreactivity of an HCV antigen for up to seven days. The reported diluent further comprises sodium phosphate, pH 6.5 (or other buffer), EDTA (or other chelator), DTT (or other reducing agent), gelatin (or other protein blocking source), ammonium thiocyanate (or other chaotrope), sodium azide (or other preservative) and SDS (or other detergent). However, the inclusion of a reducing agent in the diluent may be ineffective in or deleterious to the stability of many antigens from other microorganisms.

U.S. Pat. No. 4,956,274 concerns techniques for stabilizing peptide fragments from $\beta$-galactosidase for use in complementation assays. The solution disclosed in U.S. Pat. No. 4,956,274 contained an ionic surfactant or a surfactant derived from a sugar residue to slow degradation of $\beta$-galactosidase peptide fragments. However, the surfactants also denatured the enzyme fragments, and thus had to be removed or neutralized to enable the enzymatic fragments to return to their correct conformation and regain enzymatic activity, indicating that the solution did not stabilize the native form of the protein. The surfactants are neutralized just prior to the assay by using cyclodextrin. Alternatively, the action of the surfactants was masked with a high concentration of serum. Additional components of the disclosed reagent included a chelating agent, buffer, bacteriocide, magnesium or other ions, reducing agents, solubilizing agents such as solvents like ethylene glycol, and nonionic detergents. As those in the art will appreciate denaturing and renaturing proteins or enzyme fragments may damage some antigenic epitopes and render them inactive.

U.S. Pat. No. 5,459,033 describes a solution useful for preventing virus aggregation. The solution was reported to contain N-lauryl sarcosine or other anionic surfactants. The solution was said to enhance stability based on the supposition that virion particles, particularly, hepatitis and herpes viruses aggregate due to hydrophobic attractions thereby decreasing sensitivity. This diluent was not reported to improve or preserve the antigen's catalytic activity or immunogenicity, but to prevent aggregation. Also, before the solution could be used it reportedly had to be incubated for 15 hours to ten days at 2–35° C. to insure consistent stability, adding a major limitation to the manufacturability of the final product.

U.S. Pat. No. 5,660,978 discloses a method of stabilizing an antigen, particularly a labile protein antigen, especially an enzyme, by incorporating into a concentrated solution of antigen (such as serum), an antigen-specific antibody or portions thereof (particularly Fab) to prevent proteolysis or oxidation. Introduction of serum or non-specific IgG would not be expected to provide the desired protection or specificity of protection for such a diluent. Moreover, stabilization was completed prior to placing the antigens in a diluent. In contrast, the current invention is stabilized by the diluent itself. Additionally, the current invention stabilizes a relatively dilute solution from the beginning, not in stages as the patented invention suggests. The use of antibodies to structurally stabilize an antigen would be problematic especially if one or more of the antigenic sites are the target of an immunological assay. Additionally, one skilled in the art would have difficulty consistently producing a diluent such as the one disclosed in the '978 patent, which conformationally preserves the antigen, but does not inhibit specific enzyme activity. The invention is essentially utilizing the antibody portions as a fixative reagent, in place of a chemical fixative and thus, does not truly describe a stabilizing diluent.

Landi, S and Held, H R (Tubercle 59 (1978) 121–133) reported the addition of TWEEN® 20 (Polyoxyethylene Sorbitan Monooleate), detergent into a diluted solution and suggested that tuberculin PPD stability is was enhanced by this addition due to the detergent's anti-adsorptive properties. The tuberculin preparation, made by Connaught Laboratories, LTD., contains tuberculin PPD, 0.3% phenol (reported to act as a preservative), and 0.0005% TWEEN® 80 (Polyoxyethylene Sorbitan Monooleate) in PBS. Phenol is a hazardous material that would be unacceptable in the current invention and is likely to denature some proteins.

Despite advances in diluent formulation and lyophilization storage techniques, the need still remains for a diluent that adequately improves the long-term stability of various polypeptides and antigens, especially antigens from microorganisms, stored in solution.

SUMMARY OF INVENTION

The present invention features a reagent for stabilizing polypeptides and antigens. The reagent is especially useful for the stabilization of control or reference antigens used in analytical procedures. Antigens such as carbohydrates, proteins, polypeptides, polypeptide fragments, lipoproteins, lipopolysaccharides, polysaccharides, nucleic acids, nucleoproteins, and carbohydrates complexed with polypeptides, lipids, and other compounds are illustrative examples of the types of antigens that may be stabilized using the current invention.

The disclosed reagent surpasses previous formulations for polypeptide and antigen stability at both low and elevated temperatures. Polypeptides and antigens can be stored in the reagent in soluble form for extended periods of time at a variety of temperatures from about 0.5° C. to more than about 50° C., preferably from about 2–8° C., about room temperature (typically from about 23° C. to about 28° C., with 25° C. being particularly preferred) and about 42° C. to about 43° C., especially about 45° C. Stability at 45° C. is predictive of the reagent's ability to provide long-term antigen stability. Additionally, the disclosed reagent has the advantage of being a single aqueous solution for the purpose of stabilizing polypeptides and antigens.

In a first aspect, the invention features an aqueous reagent composition to enhance polypeptide or antigen stability. In certain preferred embodiments, the reagent comprises one or more of the following: buffer(s), blocking agent(s), solvent (s), salt(s), chelator(s), detergent(s), and preservative(s). Preferably, the reagent does not include N-dodecanoyl-N-methylglycine or decanoyl-N-methylgluconamide. The reagent may also comprise components such as tissue culture medium or commercially available diluents.

The term "buffer" as used herein refers to compositions well known to the skilled artisan that act to minimize the change in pH of a solution. Preferred buffers have a pKa that provides effective buffering at a pH of between 7 and 9. Preferred buffers are ACES, ADA, BES, bicine, bis-tris, CAPS, CHES, diethylmalonate, glycylglycine, glycinamide HCl, HEPES, HEPPS, imidazole, MES, MOPS, PIPES, POPSO, TAPSO, TES, tricine, tris, bicarbonate, and borate. Particularly preferred are phosphate buffers. Preferred buffering agent concentrations are less than 2 M; most preferred concentrations are 0.2 M, 0.1 M, 0.05 M, 0.05 M, 0.02 M, 0.01 M, 0.005, 0.001, and 0.0001 M, having a pH of 7, 7.25, 7.5, 7.75, 8, 8.25, 8.5, 8.75, and 9.

As used herein, the term "blocking agent" refers to a protein rich source containing a mixture of proteins and/or polypeptides, and that may include one or more additional components such as lipids, carbohydrates, salts, and cofactors such as heme. The term "protein rich" is defined herein. Such blocking agents can be used to stabilize one or more proteins, polypeptides, and/or antigens in the compositions and methods described herein. Preferred blocking agents have a pH of between about 6.5 and about 8.0, and/or an osmolality of between about 250 and about 350 mOsm/Kg $H_2O$. Particularly preferred blocking agents are sera, such as horse serum, newborn calf serum, calf serum, adult bovine serum, human serum, rabbit serum, sheep serum, etc., and serum replacements known to the skilled artisan. Most preferred as a blocking agent is fetal calf serum.

The term "protein rich" as used herein refers to a solution containing a mixture of proteins and/or polypeptides, and having a total protein concentration between about 1 g % and about 50 g %, most preferably between about 3 g % and about 10 g %. For example, fetal calf serum has a total protein content of between about 3 g % and about 4.5 g %, while adult bovine serum has a total protein content of between about 4.5 g % and about 8.5 g %.

The terms "solvent" and "solubilizing agent" as used herein refer to a liquid substance capable of dispersing the other components of the composition. Preferred solvents are water, glycerol, DMSO, alcohols such as ethanol, methanol, etc., acetone, dimethyl sulfoxide, acetonitrile, and dimethyl formamide.

The term "salt" as used herein refers to one or more compounds that result from replacement of part or all of the acidic hydrogen of an acid by a metal, or an element acting like a metal. Preferred salts are KCl, NaCl, $MgCl_2$, $MgSO_4$, and $CaCl_2$. Preferred salt concentrations are between 4M and 0.1 mM, most preferably between 2M and 50 mM.

The term "chelator" as used herein refers to a molecule that binds metal ions, usually by binding to two or more complexing groups within the molecule. Chelators are well known in the art, and include certain proteins and polypeptides, as well as small molecules such as ethylenediaminetetraacetic acid (EDTA) and ethylene glycol-bis(β-aminoethyl ether)-N,N,N',N'-tetraacetic acid (EGTA). Preferred chelator concentrations are between 100 mM and 0.01 mM, most preferably between 20 mM and 1 mM.

The term "detergent" as used herein refers to compounds well known in the art that are able to emulsify oils and act as wetting agents. Preferred detergents include CHAPS, cholic acid, deoxycholic acid, digitonin, n-dodecyl-β-D-maltoside, glycodeoxycholic acid, n-lauroylsarcosine, lauryl sulfate, saponin, TWEEN® 20 (Polyoxyethylene Sorbitan Monolaurate), and TWEEN® 20 (Polyoxyethylene Sorbitan Monolaurate). Preferred detergent concentrations are between of about 0.001% to about 5%. Most preferably, the composition comprises about 0.01%, 0.02%, 0.03%, 0.04%, 0.05%, 0.06%, 0.07%, 0.08%, 0.09%, 0.1%, 0.2%, 0.3%, 0.4%, 0.5%, 1.0%, and 2%.

The term "preservative" as used herein refers to compounds well known to the skilled artisan that prevent the growth of microorganisms. Preferred preservatives include thimerosal, sorbic acid, BHA, BHT, MICROCIDE II® (trimethyltetradecylammonium bromide) and antibiotics such as gentamycin, penicillin, streptomycin, etc. Preferred preservative concentrations are between 10% and 0.001 mM, most preferably between 1% and 0.1%.

As used herein "polypeptide" refers to a polymer of amino acids and does not refer to a specific length of the product, thus, peptides, oligopeptides, proteins, and fragments thereof are included within the definition. The term "polypeptide" does not exclude, post-translational modifications of the polypeptide, for example, glycosylation, acetylation, phosphorylation, and the like.

As used herein "antigens" include carbohydrates, proteins, polypeptides, lipoproteins, lipopolysaccharides, polysaccharides, nucleic acids, and carbohydrates complexed with polypeptides, lipids, and other compounds. Antigens may be capable of eliciting an immune response in an animal having a functional immune system. In a preferred embodiment, the antigens stabilized are polypeptide antigens. These polypeptide antigens may be found alone or in association with other molecules. In a particularly preferred embodiment, the polypeptide stabilized are nucleoprotein antigens. Nucleoprotein antigens may be from any number of sources and may be found alone or in association with other molecules.

By "nucleoprotein antigens" is meant any polypeptide found associated with or attached to a nuclear complex.

A particularly preferred nucleoprotein is a nucleoprotein from influenza virus, particularly influenza type B.

By "antigen stability" is meant the ability to maintain a consistent signal generated by one reagent, in an assay or analytical method, especially a diagnostic assay or an immunoassay, after reagent storage for a given period of time at a set temperature. Typical storage temperatures are from about 2°–30° C. Antigen stability can also be assessed by measuring antigen deterioration at elevated temperatures for a shorter period of time. Typical temperatures for accelerated stability tests are from about 30° to 60° C.

By "microorganisms" is meant a prokaryote, eukaryote such as yeast, virus, prion or other infectious particle.

By "analytical method" is meant any technique that allows specific detection of one or more antigens. Analytical methods include immunoassays of any detection format and nucleic acid hybridization, numerous examples of which are known in the art. A particularly preferred optical immunoassay method is described in U.S. Pat. Nos. 5,550,063; 5,955, 377; and 5,541,057.

In a second aspect, the invention features an aqueous reagent composition to enhance antigen or polypeptide stability wherein the antigen is from a microorganism. In a preferred embodiment, the microorganisms comprise viruses and/or bacteria. The invention is particularly preferred for use with viral analytes. In a most particularly preferred embodiment, the invention features a reagent composition for stabilizing antigens and polypeptides from influenza, especially polypeptides and antigens from influenza B.

In a third aspect, the invention features a reagent composition for stabilizing a nucleoprotein of influenza virus, particularly nucleoprotein from influenza B.

In a fourth aspect, the invention features an aqueous reagent composition for stabilizing an antigen preparation to be used as a control or reference reagent associated with an analytical method.

In a particularly preferred embodiment, the reagent comprises a buffer, a blocking agent, a salt, a chelator, a solubilizing agent, a non-ionic detergent, and a preservative. Most preferably, the reagent does not contain N-dodecanoyl-N-methylglycine or decanoyl N-methylgluconamide.

In further preferred embodiments, the reagent may also contain tissue culture media, STABILCOAT® buffer (an aqueous solution containing purified bovine protein and other non-toxic chemicals in phosphate buffered saline, pH 7.0–7.4; BSI, Inc.), and formalin-inactivated virus-containing cell culture media.

In yet other preferred embodiments, the reagent comprises sodium phosphate buffer, fetal calf serum, glycerol, sodium chloride, EDTA, TWEEN® 20 detergent (polyoxyethylene sorbitan monolaurate), MICROCIDE II® (trimethyltetradecylammonium bromide). Gentamycin Sulfate, and may contain sucrose, tissue culture media and STABILCOAT® buffer (an aqueous solution containing purified bivine protein and other non-toxic chemicals in phosphate buffered saline, pH 7.0–7.4; BSI, Inc.). The pH of the solution is between about 7 and about 9, most preferably between 7.5 and 8.5. One skilled in the art understands that similar reagents can substitute for those listed above. For example, EDTA can be replaced with EGTA, and MICROCIDE II® (trimethyltetradecylammonium bromide), or gentamycin can be replaced by other anti-bacterial agents. Preferred concentrations of the above listed reagents are as follows: for sodium phosphate, 0.1 mM to 1000 mM, more preferably 1 mM to 200 mM, most preferably 50 mM to 100 mM; for fetal calf serum, 0.1% to 40% v/v, most preferably 2% to 20% v/v; for glycerol, 0.1% to 30% v/v, most preferably 2.5% to 10% v/v; for sodium chloride, 0.1 mM to 4 M, most preferably 50 mM to 2 M; for EDTA, 0.01 mM to 100 mM, more preferably 1 mM to 20 mM, most preferably 10 mM to 15 mM; for TWEEN® 20 (Polyoxyethylene Sorbitan Monolaurate), 0.001% to 1%, more preferably 0.01% to 0.1%, most preferably 0.5%; for MICROCIDE II® (trimethyltetradecylammonium bromide), 0.001% to 1% w/v, most preferably 0.002% to 0.1% w/v; for gentamycin sulfate, 0.01% to 10% w/v; more preferably 0.1% to 2.5%, most preferably 0.25% to 1%; and for sucrose, 0.01% to 5% w/v, most preferably 0.1% to 0.5%.

In especially preferred embodiments, the diluent comprises an amount greater than or equal to about: 50 mM sodium phosphate; 2% v/v fetal calf serum; 10% v/v glycerol; 50 mM sodium chloride; 10 mM EDTA; 0.05% v/v TWEEN® 20 (Polyoxyethylene Sorbitan Monolaurate) detergent; 0.01% w/v MICROCIDE II® (trimethyltetradecylammonium bromide) preservative; and 0.5% w/v gentamycin sulfate. The reagent may also comprise up to 0.5% sucrose, 15% STABILCOAT® buffer (an aqueous solution containing purified bovine protein and other non-toxic chemicals in phosphate buffered saline, pH 7.0–7.4; BSI, Inc.) and 20% tissue culture medium from the antigen preparation or by separate addition. The preferred pH of the solution is between about 7.5 to about 8.5. It may also be possible to replace the buffer and/or salt with a concentration of pre-formulated tissue culture medium (for example, Eagle's Minimum Essential Media or Dulbecco's Modified Eagle Media from BioWhittaker).

In a fifth aspect, the invention features methods for stabilizing polypeptides and antigens derived from microorganisms. In a preferred embodiment said method is used for stabilizing an antigen preparation from a microorganism for use as a control or reference reagent associated with an analytical method or for use in a pharmaceutical preparation.

DETAILED DESCRIPTION OF THE PREFERRED EMBODIMENTS

A. Introduction

Figure 1:
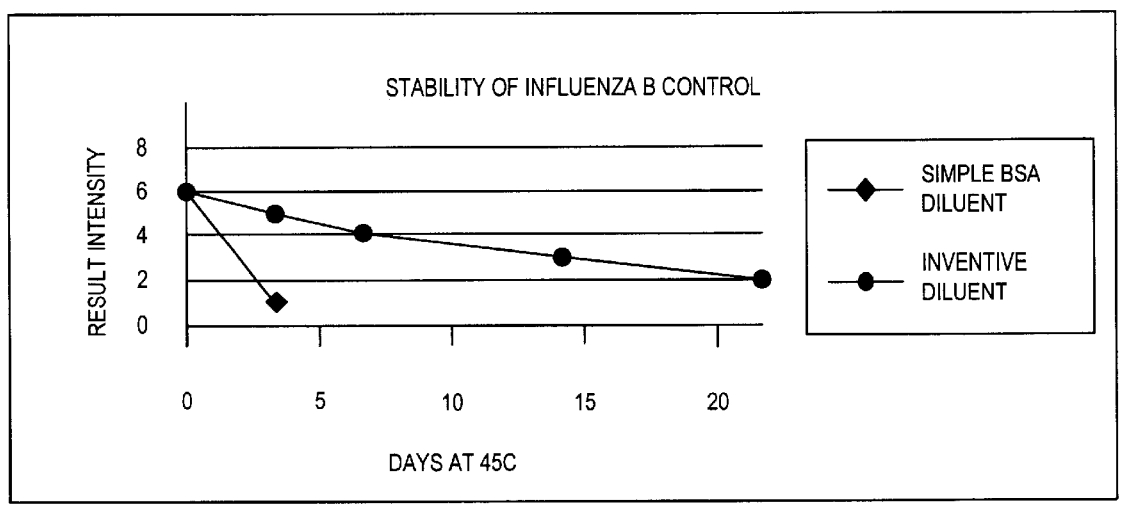
FIG. 1 shows the advantages of the diluent of this invention on the stability of inactivated influenza B.

For ease in understanding the current invention, the development of the reagent composition is described for a specific application, namely stabilizing influenza-derived antigens. However, the general utility of the stabilizing reagent composition can be demonstrated for other antigens or polypeptides by conducting similar experiments.

During the development of reagents for diagnostic assay components or other uses, a determination of a reagent's long-term stability is required. Initially, accelerated stability validations are completed for assessment of a reagent's shelf-life prior to the completion of real-time stability determination. Accelerated stability studies can be performed quickly and are often used by those skilled in the art to predict stability. One means of doing this is to incubate the reagent at elevated temperatures and assay at relatively short time intervals. For example, incubations for 3 to 7 days at 37° C., 45° C., and other elevated temperatures are analyzed using the Arrhenius equation to predict whether a reagent will remain stable at about 2°–8° C. for long periods of time. This method is currently believed to be most accurate at predicting reagent failure. If a reagent is unable to withstand an elevated temperature challenge, it is not likely to be stable for an extended time under normal storage conditions. Elevated temperature stability is less predictive of long-term stability, as it does not accurately predict rate of decay, but it does give an indication of stability by identifying a probable point of reagent failure. As the loss of stability at elevated temperatures decreases, so does the likelihood of real-world failure.

In addition to accelerated validation, real-time, long-term studies are also necessary to assess a reagent's potential to stabilize polypeptides or antigens. Conditions for real-time studies are known to those skilled in the art. For example, real-time assessment conditions may include storing the reagent at normal storage temperatures of about 2°–8° C. or at room temperature (18°–30°C.) until the point of reagent failure is reached.

In the development of positive control reagents for an immunoassay for influenza viruses both formalin-inactivated influenza A and B type viruses were assessed for their stability in a protein-based diluent. Where the epitope detected in the assay is from the viral nucleoprotein, inactivated influenza A was significantly more stable in simple diluents and commercially available stabilizing diluents than was inactivated influenza B. To insure commercial viability of a new product for influenza A and B detection, a means of stabilizing inactivated influenza B was required. A diluent was formulated which imparts stability on both types of inactivated influenza viral suspensions. This diluent has demonstrated the ability to improve the stability of inactivated influenza B virus, in solution, for longer periods of time than previous diluent formulations.

Influenza A has been shown to be stable in simple protein based diluents. One such diluent contains bovine serum albumin (BSA) and TWEEN® 20 (Polyoxyethylene Sorbitan Monolaurate) detergent in phosphate buffered saline (PBS) otherwise called PBT. A second formulation is a commercial product, STABILCOAT® buffer (an aqueous solution containing purified bovine protein and other non-toxic chemicals in phosphate buffered saline, pH 7.0–7.4; BSI, Inc.), and has also been demonstrated to stabilize influenza A. However, neither of these solutions was able to stabilize influenza B. It is likely that the monoclonal antibodies that detect the different strains in the assays performed recognize different epitopes on the two nucleoproteins. These epitopes may be affected differently by inactivation and storage conditions. Additionally, the immunogens used in the initial preparations for the monoclonal antibodies used in an assay may have been prepared differently and thus, may have favored the production of monoclonals that recognize differently conformed epitopes. We believe that the diluent compositions described herein have similar stabilizing effects on inactivated influenza A nucleoprotein as it does on inactivated influenza B nucleoprotein. In addition, other viral and bacterial proteins are thought to be stabilized as well.

It should be noted that inherent in the process of viral inactivation and dilution into each of the diluent formats is the incorporation of the components of the inactivated viral stock suspensions. The inactivated viral stock suspension is composed of 50% formalin-inactivated virus-containing cell culture media (ICC) and 50% STABILCOAT® buffer (an aqueous solution containing purified bovine protein and other non-toxic chemicals in phosphate buffered saline, pH 7.0–7.4; BSI, Inc.). Each of the positive control compositions tested comprise some volume of this stock suspension.

B. Formation of New Diluent

The formulation of a new diluent began with the simple protein diluent, PBT, comprising BSA, TWEEN® 20 (Polyoxyethylene Sorbitan Monolaurate), and PBS solution. Each of the components was evaluated for their ability to stabilize inactivated influenza B virus while maintaining or enhancing the stability of inactivated influenza A virus. An increase in stability of the antigen preparation was assessed in the following manner. Inactivated viral materials were diluted to a desired strength of signal intensity for the analytical testing method with which the control reagent will be marketed. Generally, a low to medium signal strength is selected for the control reagent on its corresponding analytical method. The various reagent compositions at the selected antigen dilution are tested immediately in the appropriate analytical method. The various reagent compositions (containing antigen) are placed at various storage conditions and then periodically re-tested in the analytical method. Reagent compositions that retain the original signal or have only minimal degradation of the original signal strength over the range of storage conditions are determined to provide enhanced stability. Signal strength may be assessed qualitatively, quantitatively, visually, or by instrumentation. During the component selection process, several modifications were made to the PBT diluent. First, a different blocking agent, such as fetal calf serum was substituted for BSA. Next, a solubilizing agent such as glycerol and a chelator, such as EDTA or EGTA, were added to enhance stability. Additionally, it was determined that the inclusion of a non-ionic detergent, such as TWEEN® 20 (Polyoxyethylene Sorbitan Monolaurate), detergent was essential for stability. Preservatives such as a combination of MICROCIDE II® (trimethyltetradecylammonium bromide) and Gentamycin sulfate were included as antimicrobial agents.

In a particularly preferred embodiment, the inventive diluent comprises an amount greater than or equal to: 50 mM sodium phosphate, 2% v/v fetal calf serum, 1% v/v glycerol, 50 mM sodium chloride, 5 mM EDTA, 0.05% v/v TWEEN® 20 (Polyoxyethylene Sorbitan Monolaurate) detergent, 0.01% w/v quaternary ammonium compound, and 0.5% w/v gentamycin sulfate. The reagent may also comprise up to 15% STABILCOAT® buffer (an aqueous solution containing purified bovine protein and other non-toxic chemicals in phosphate buffered saline, pH 7.0–7.4; BSI, Inc.) 20% tissue culture medium from the antigen preparation or by separate addition. The preferred pH of the solution is between about 7.5 to about 8.5. It may also be possible to replace the buffer and/or salt with a concentration of preformulated tissue culture medium (for example, Eagle's Minimum Essential Media or Dulbecco's Modified Eagle Media from BioWhittaker).

Not wishing to be bound by any particular theory, the modifications to the original diluent may enhance polypeptide or antigenic stability by the following mechanisms. Fetal calf serum may provide a richer protein source than BSA, as it is a total serum product instead of purified protein. It may comprise other stabilizing materials. Glycerol may increase hydration of the antigen via hydrogen bonding. The chelator may increase stability by removing cations, which may negatively impact the polypeptide or antigen itself, or which may be necessary for the activity of certain degradative enzymes that could damage the antigen or polypeptide or may inhibit catalytic sites on the antigen. The detergent may maintain important secondary structures and supportive associations of the antigen or polypeptide, while disrupting unimportant or degradative structures/interactions.

The current invention was assessed by first benchmarking antigen stability in a simple BSA protein diluent (PBT), described above. Typically, in reagent development, the retention of positivity to about 3 days at 45° C. is adequate to assess long-term stability at lower temperatures. Those skilled in the art believe that stability of up to about 14 days at elevated temperature indicates a well-stabilized antigen. In addition, the longer time a reagent retains activity at 45° C.; the longer it is likely to be stable at lower temperatures, such as at about 2°–8° C. and at room temperature. First, formalin-inactivated influenza suspension stocks were made in a manner commonly known in the art and described in Example 1 below. Then, both influenza A and influenza B inactivated stocks were spiked into the simple protein diluent at a 1:2 and 1:4 dilution, respectively. At these dilutions, the test diluent contained, in its entirety, 50% diluent, 25% ICC, and 25% Stabilcoat buffer or 75% diluent, 12.5% ICC, and 12.5% STABILCOAT® buffer (an aqueous solution containing purified bovine protein and other non-toxic chemicals in phosphate buffered saline, pH 7.0–7.4; BSI, Inc.), respectively. These antigen dilutions were selected to supply a moderate positive signal on visual inspection of a reacted test device. The two resulting solutions were tested at Day 0, Day 3 at 4° C., and Day 3 at 45° C. with the FLU OIA® test kit (Biostar, Inc.) for positivity. Tests were performed as per the package insert. Inactivated influenza B lost all positivity on Day 3 at 45° C. and inactivated influenza A lost a portion of its positivity. Tests were not run on subsequent timepoints due to the failure of the reagent. The PBT protein diluent failed to maintain the antigen's stability to the desired degree.

In addition, STABILCOAT® buffer (an aqueous solution containing purified bovine protein and other non-toxic chemicals in phosphate buffered saline, pH 7.0–7.4; BSI, Inc.), a commercially available diluent that is formulated to protect and stabilize antibody coated surfaces, was tested using the antigen dilutions described above. The STABILCOAT® (an aqueous solution containing purified bovine protein and other non-toxic chemicals in phosphate buffered saline, pH 7.0–7.4; BSI, Inc.)-derived control reagent's stability was assessed as above with the exception that the test points were Day 0 and Day 4 (4° and 45° C. storage conditions). Under these conditions the diluent's complete composition was 75% STABILCOAT® buffer (an aqueous solution containing purified bovine protein and other non-toxic chemicals in phosphate buffered saline, pH 7.0–7.4; BSI, Inc.) and 25% ICC. Even in the presence of tissue culture media, STABILCOAT® (an aqueous solution containing purified bovine protein and other non-toxic chemicals in phosphate buffered saline, pH 7.0–7.4; BSI, Inc.) was unable to maintain the stability of inactivated influenza B antigen beyond Day 4, indicating its lack of long-term storage potential.

Next, the current invention's reagent composition was tested as above to assess its performance. In this case, the diluent's complete composition contained 50% diluent, 25% ICC, and 25% STABILCOAT® buffer (an aqueous solution containing purified bovine protein and other non-toxic chemicals in phosphate buffered saline, pH 7.0–7.4; BSI, Inc.) for inactivated influenza A and 75% diluent, 12.5% ICC, and 12.5% STABILCOAT® buffer (an aqueous solution containing purified bovine protein and other non-toxic chemicals in phosphate buffered saline, pH 7.0–7.4; BSI, Inc.) for inactivated influenza B solutions. At Day 3 at 45° C., both inactivated influenza A and B lost some positivity but were still clearly positive. The inactivated influenza B reagent was evaluated at Day 7, Day 14, and Day 21. Eventually, after 21 days at 45° C., inactivated influenza B lost all positivity. Previous studies have shown that inactivated influenza A loses a significant portion of its positivity by Day 21 as well. The enhancement of inactivated influenza A under these particular assay conditions is not shown in the data because it was not tested to failure. However, the stability of inactivated influenza A under these conditions could be very high and extend beyond the timepoints tested. If tested to failure under these or other assay conditions, the inventive diluent should enhance the stability of the influenza A antigen as well. Thus, relative to the simple PBT protein diluent and STABILCOAT® (an aqueous solution containing purified bovine protein and other non-toxic chemicals in phosphate buffered saline, pH 7.0–7.4; BSI, Inc.), the composition of the current invention is much better able to stabilize antigens in solution for storage.

In another assessment of the current invention, the inventive stabilizing diluent was utilized in a more sensitive optical assay method. The positive control for this method uses antigens diluted to a 1:10 dilution of both formalin-inactivated influenza A and formalin-inactivated influenza B to achieve the moderate signal necessary for such a control solution. Antibodies used in this evaluation were selected based on optimal analytical performance for the type of surface used. Reactive areas on the assay surfaces were made in a preferred method by striping monoclonal anti-influenza A antibody or monoclonal anti-influenza B antibody onto the surface such that each assay surface contained one influenza A reactive area and one influenza B reactive area. The surfaces were dried and overcoated with a preservative solution at room temperature. Antibody surfaces were heat-sealed using heat-staking equipment to a polystyrene ring that allows solution to flow through or around the porous surface. The plastic ring supplies support to facilitate handling and a means to mount the porous surface onto a vacuum source to assist in removal of fluids from and drying of the porous surface. For the purpose of this experiment, assays were conducted in a flow-through manner. Flow-through indicates that sample contacted the assay surface and flowed through, over, or around it during the assay procedure.

This experiment tested the ability of the cell culture media (EMEM, BioWhittaker Cat. #12 136Q)to enhance stability of the antigens as a component of the inventive stabilizing diluent. Four test solutions were made: (A) 75% inventive diluent, 12.5% EMEM and 12.5% STABILCOAT® buffer (an aqueous solution containing purified bovine protein and other non-toxic chemicals in phosphate buffered saline, pH 7.0–7.4; BSI, Inc.), (B) solution A, where the EMEM additionally contains 2% FCS, 1% L-Glutamine, and 0.5% PenStrep/Fungizone (an antimicrobial solution, BioWhittaker Cat. #17–745H), (C) 75% inventive diluent and 25% Stabilcoat diluent, and (D) inventive diluent only. A 1:10 dilution of inactivated influenza B stock suspension was made in each of the four diluents by first making a 1:4 dilution and subsequently a 1:2.5 dilution with the respective test diluent. Each solution was tested at Day 3 at 4° C. and Day 3 at 45° C. Solution A showed the best stability at 3 days at 45° C., followed by solution B, D and C. The results indicate that incorporating cell culture media/STABILCOAT® (an aqueous solution containing purified bovine protein and other non-toxic chemicals in phosphate buffered saline, pH 7.0–7.4; BSI, Inc.) into the diluent under increasingly dilute antigen conditions enhances the stability of the antigen (compare stability in solution A to that of solution D). Utilizing a higher concentration of STABIL-COAT® buffer (an aqueous solution containing purified bovine protein and other non-toxic chemicals in phosphate buffered saline, pH 7.0–7.4; BSI, Inc.) as the only other constituent (solution C) proved deleterious to the antigen's stability (relative to solution A).

Therefore, these results clearly indicate that the current invention greatly surpasses other diluents of its type in its ability to stabilize protein antigens in an aqueous medium, especially those of influenza.

The following examples are offered by way of illustration, not by way of limitation and are for further illustrating various aspects and embodiments of the present invention. The examples are in no way intended to be limiting in scope.

EXAMPLES

Example 1

Antigen stability was assessed in a simple protein diluent (PBT) comprising 1× Dulbecco's PBS, 0.05% MICRO-CIDE II® (trimethyltetradecylammonium bromide), 2% BSA, 0.01% TWEEN® 20 (Polyoxyethylene Sorbitan Monolaurate) preservative, and 0.5% gentamycin sulfate. First, inactivated influenza viral suspension stocks were prepared as follows. Confluent MDCK p83 cells were infected with either influenza A (1:10,000 dilution of A/Hong Kong 68 per flask) or influenza B (1:1000 dilution of B/Panama 45/90 per flask) and grown in Eagle's MEM maintenance medium (with 2% heat-inactivated FCS, 1% L-Glutamine, and 0.5% Pen/Strep/Fungizone) until 90–100% CPE (cytopathic effect) was observed. Virus was harvested by vortexing and then centrifuging the cell suspension. The resulting supernatant was inactivated by adding 37% formaldehyde solution (Sigma Chemical, F-1268) to 0.2% of the total volume (2 µl/ml) and incubating at room temperature for 1 hour. Then, the virus-containing solution was mixed with equal amounts of STABILCOAT® buffer (an aqueous solution containing purified bovine protein and other non-toxic chemicals in phosphate buffered saline, pH 7.0–7.4; BSI, Inc.), aliquoted, and used or frozen immediately.

The inactivated influenza A and influenza B viral suspension stocks were spiked into the simple BSA diluent at 1:2 and 1:4, respectively, by adding 1 ml inactivated influenza A stock to 1 ml of the simple diluent, and in a separate container 0.5 ml inactivated influenza B stock to 1.5 ml of the simple diluent. At these dilutions, the test diluent contained, in its entirety, 50% diluent, 25% ICC, and 25% STABILCOAT® buffer (an aqueous solution containing purified bovine protein and other non-toxic chemicals in phosphate buffered saline, pH 7.0–7.4; BSI, Inc.) or 75% diluent, 12.5% ICC, and 12.5% STABILCOAT® buffer (an aqueous solution containing purified bovine protein and other non-toxic chemicals in phosphate buffered saline, pH 7.0–7.4; BSI, Inc.), respectively. Next, each resulting solution was tested at Day 0 with the FLU OIA® test kit (Biostar, Inc.) for positivity. Tests were performed as per the package insert and signal quality or positivity was assessed by visual interpretation of the reacted FLU OIA test device as follows: (0) negative; (1) shadow; (2) very weak positive; (3) positive between very weak and weak; (4) weak positive; (5) positive between weak and moderate; (6) moderate positive; (7) positive between moderate and strong; (8) strong positive result. A signal was deemed positive if it was ranked from 2–8.

After dilution each solution was split into two portions. One was stored at 4° C. and one at 45° C. for 3 days. All four solutions were retested at Day 3 in the same manner as on Day 0. Day 0 and 4° C. controls resulted in the expected moderate positive signals. Inactivated influenza B lost all positivity on Day 3 at 45° C., and inactivated influenza A lost a portion of its positivity. Tests were not run in subsequent timepoints due to the failure of the reagent. Typically, in reagent development, the retention of positivity to 3 days at 45° C. is adequate to assess long-term stability at lower temperatures. The longer time a reagent retains activity at 45° C.; correlates with stability at lower temperatures, such as 2°–8° C. and at room temperature. Thus, this simple PBT formulation failed to maintain the stability of the antigen to the desired degree.

Example 2

STABILCOAT® buffer (an aqueous solution containing purified bovine protein and other non-toxic chemicals in phosphate buffered saline, pH 7.0–7.4; BSI, Inc.), a commercially available diluent that is formulated to protect and stabilize antibody coated surfaces, was tested as described in Example 1 with the exception that the reagent was tested Day 0 and Day 4 (4° and 45° C. storage conditions). Note that the diluent's complete composition was 75%

STABILCOAT® (an aqueous solution containing purified bovine protein and other non-toxic chemicals in phosphate buffered saline, pH 7.0–7.4; BSI, Inc.) and 25% ICC. Stabilcoat was unable to maintain the stability of inactivated influenza B antigen beyond Day 4 as well, indicating its lack of long-term storage potential.

Example 3

Next, the current invention's reagent composition was tested in a similar experiment as described in Example 1. The diluent was made in a 20 ml volume as follows. To a conical tube, 2 mls of 1 M sodium phosphate buffer and 8 mls dH$_2$O were added (100 mM), mixed, and the pH was adjusted to 7.5. Next, 0.175 g NaCl (150 mM) was added and mixed. Then, 0.1 ml of a 10% TWEEN® 20 (Polyoxyethylene Sorbitan Monolaurate) solution (0.05%) was added and mixed. Next, 0.2 ml of a 1% stock of MICROCIDE II® (trimethyltetradecylammonium bromide) preservative (0.01%) and 0.1 ml of gentamycin sulfate (0.5%) were added to the tube and mixed well. Next, 2 mls of glycerol (10%) and 1 ml fetal calf serum (5%) were added and mixed. Then, 0.4 ml of a 500 mM stock of a EDTA/ dH$_2$O (10 mm), mixture was added and mixed and pH was adjusted to 7.5. The total volume was brought up to 20 mls with dH$_2$O.

The viral test reagents were made by adding 5 mls of the diluent to 5 mls of the inactivated influenza A virus stock (a 1:2 dilution) or 7.5 mls of the diluent to 2.5 mls of the inactivated influenza B virus stock (a 1:4 dilution) and mixed well. In this case, the diluent's complete composition contained 50% diluent, 25% ICC, and 25% STABILCOAT® buffer (an aqueous solution containing purified bovine protein and other non-toxic chemicals in phosphate buffered saline, pH 7.0–7.4; BSI, Inc.) for inactivated influenza A and 75% diluent, 12.5% ICC, and 12.5% STABILCOAT® buffer (an aqueous solution containing purified bovine protein and other non-toxic chemicals in phosphate buffered saline, pH 7.0–7.4; BSI, Inc.) for inactivated influenza B solutions. The FLU OIA test was performed as per the package insert for each test reagent at each throughout the study. This experiment was carried out to 21 days due to enhancement of the stability of the antigens. At Day 3 at 45° C., both inactivated influenza A and B lost some positivity but were still clearly positive. The inactivated influenza B reagent was evaluated at Day 7, Day 14, and Day 21. Eventually, on Day 21 at 45° C., inactivated influenza B lost all positivity. Inactivated influenza A has been shown in other studies to lose a significant portion of its activity after this amount of time as well. Assay results were interpreted visually, based on a subjective scale of 0–8 as follows: (0) negative; (1) shadow; (2) very weak positive; (3) positive between very weak and weak; (4) weak positive; (5) positive between weak and moderate; (6) moderate positive; (7) positive between moderate and strong; (8) strong positive result. A signal was deemed positive if it was ranked from 2–8. The enhanced stability of influenza B in the inventive diluent is shown in FIG. 1.

Example 4

In another assessment of the current invention, the stabilizing diluent was utilized in a different assay where the positive control used antigens diluted to a 1:10 dilution of both formalin-inactivated influenza A and formalin-inactivated influenza B to achieve the moderate signal necessary for such a control solution. The inactivated viral suspension stocks were prepared as in Example 1 and the stabilizing diluent as described in Example 3. Antibodies were selected to coat optically prepared porous surfaces where the surface was a track-etched polycarbonate membrane coated with an optical layer of silicon to provide reflectivity, an anti-reflective layer of Si$_3$N$_4$, and an attachment layer of diamond-like carbon per WO/98/18962. Antibodies used in this evaluation were selected based on optimal analytical performance for the type of surface used. Reactive areas on the assay surfaces were made in a preferred method by striping monoclonal anti-influenza A antibody (40 µg/ml in 0.1 M HEPES, pH 8.0, 1% sucrose) or monoclonal anti-influenza B antibody (40 µg/ml in 0.1 M HEPES, pH 8.0, 1% sucrose, 150 mM NaCl) onto the surface such that each assay surface contained one influenza A reactive area and one influenza B reactive area. The surfaces were striped with a BIOJECT® instrument (BioDot, Inc.), dried and overcoated with a preservative solution at room temperature. Antibody surfaces were heat-sealed using heat-staking equipment to a polycarbonate ring that allows solution to flow through or around the porous surface. The plastic ring supplies support to facilitate handling and a means to mount the porous surface onto a vacuum source to assist in removal of fluids from and drying of the porous surface. The coated surfaces were stored at 2–8° C. prior to use. For the purpose of this experiment, assays were conducted in a flow-through manner. Flow-through indicates that sample contacted the assay surface and flowed through, over, or around it during the assay procedure.

This experiment tested the ability of the cell culture media (EMEM) to enhance stability of the antigens as a component of the inventive stabilizing diluent. Four test solutions were made: (A) 75% inventive diluent, 12.5% EMEM and 12.5% STABILCOAT® buffer (an aqueous solution containing purified bovine protein and other non-toxic chemicals in phosphate buffered saline, pH 7.0–7.4; BSI, Inc.), (B) solution A, where the EMEM additionally contains 2% FCS, 1% L-Glutamine, and 0.5% PenStrep/Fungizone, (C) 75% inventive diluent and 25% STABILCOAT® diluent (an aqueous solution containing purified bovine protein and other non-toxic chemicals in phosphate buffered saline, pH 7.0–7.4; BSI, Inc.), and (D) inventive diluent only. A 1:10 dilution of inactivated influenza B stock suspension was made in each of the four diluents by first making a 1:4 dilution and subsequently a 1:2.5 dilution. Each of the four solutions (30 µl) were added to individual tubes containing 165 µ of an extraction reagent and incubated for 1 minute. The entirety of each sample was transferred onto the surface described above and incubated for 3 minutes. Then, 100 µl of a conjugate (anti-influenza A antibody conjugated to HRP mixed with an anti-influenza B antibody conjugated to HRP) was placed onto the surface for 3 additional minutes. Next, vacuum was applied to the bottom of the surface to draw the sample/conjugate mix through and away from the surface. The surface was washed 3 times by placing an aqueous wash solution on the surface and allowing it to flow through the surface until it was dry while under vacuum pressure. The vacuum was turned off and 75 µl of a precipitating TMB substrate was placed onto the assay surface and incubated for 6 minutes. The substrate was pulled through the surface and the surface was washed once and dried as described above. Then the assay signals were interpreted as in Example 3.

Figure 2:
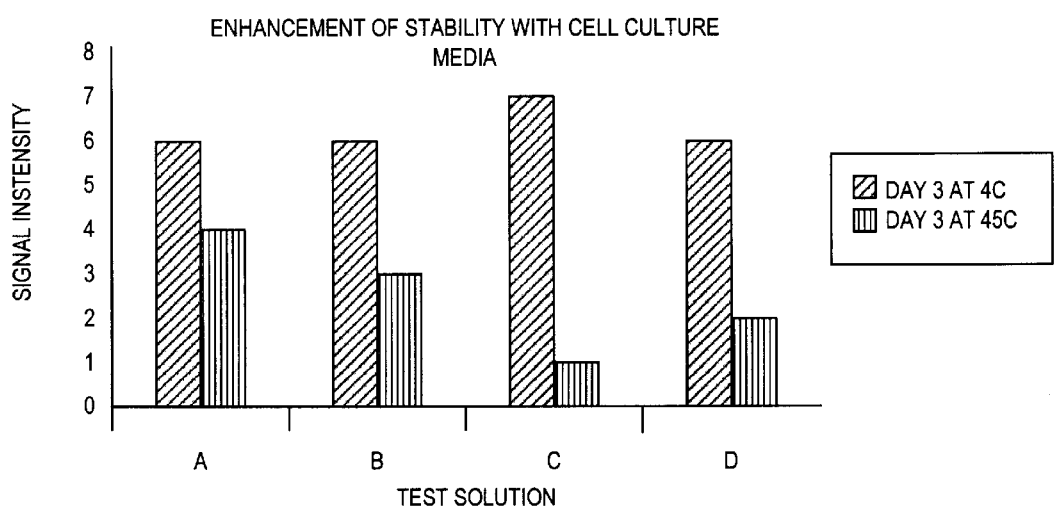
FIG. 2 shows the ability of cell culture media to further enhance the stabilizing properties of the diluent of the invention.

Each solution was tested at Day 3 at 4° C. and Day 3 at 45° C. Solution A showed the best stability at 3 days at 45° C., followed by solution B, D, and C. The results indicate that incorporating the cell culture media/STABILCOAT® diluent (an aqueous solution containing purified bovine protein and other non-toxic chemicals in phosphate buffered saline, pH 7.0–7.4; BSI, Inc.) into the diluent under increasingly dilute antigen conditions enhances the stability of the antigen (compare stability in solution A to that of solution D). Utilizing a higher concentration of STABILCOAT® buffer (an aqueous solution containing purified bovine protein and other non-toxic chemicals in phosphate buffered saline, pH 7.0–7.4; BSI, Inc.) as the only other constituent (solution C) proved deleterious to the antigen's stability. FIG. 2 shows the results obtained for the preceding experiment.

These results clearly indicate that the current invention greatly surpasses other diluents in its ability to stabilize protein antigens in an aqueous solution, especially those of influenza. Each reference, patent, or patent application referred to above is hereby incorporated by reference in its entirety.

While a preferred embodiment of the present invention has been described, one skilled in the art would understand that various changes, adaptations and modifications may be made therein without departing from the spirit of the invention and the scope of the appended claims.

We claim:

1. An aqueous reagent composition comprising a buffer, a serum, glycerol, a salt selected from the group consisting of potassium chloride, sodium chloride, magnesium chloride, magnesium sulfate, and calcium chloride, a chelating agent selected from the group consisting of EGTA and EDTA, a detergent selected from the group consisting of CHAPS, cholic acid, deoxycholic acid, digitonin, n-dodecyl-β-D-maltoside, glycodeoxycholic acid, n-lauroylsarcosine, lauryl sulfate, saponin, polyoxyethylene sorbitan monooleate, and polyethylene glycol P-1,1,3,3-tetramethylbutylphenyl ether, and a preservative at a final pH of 7.5 to 8.5, wherein said composition does not comprise N-dodecanoyl-N-methylglycine or decanoyl N-methylgluconamide.

2. The aqueous reagent of claim 1, wherein said serum is fetal calf serum.

3. The aqueous reagent of claim 1, wherein said salt is sodium chloride.

4. The aqueous reagent of claim 1, wherein said chelating agent is EDTA.

5. The aqueous reagent of claim 1, wherein said detergent is polyoxyethylene sorbitan monooleate.

6. The aqueous reagent of claim 1, wherein said preservative is trimethyltetradecylammonium bromide and gentamycin.

7. The aqueous reagent of claim 1, wherein said buffer is sodium phosphate.

8. The aqueous reagent of claim 1, wherein said buffer is sodium phosphate, said serum is fetal calf serum, said salt is sodium chloride, said chelator is EDTA, said detergent is polyoxyethylene sorbitan monooleate and said preservative is trimethyltetradecylammonium bromide and gentamycin.

9. The aqueous reagent of claim 1, further comprising a tissue culture medium or tissue culture media.

10. The aqueous reagent of claim 8, wherein said tissue culture medium is Eagle's minimum essential media.

11. The aqueous reagent of claim 1, wherein the aqueous reagent comprises between 50 mM and 100 mM sodium phosphate, between 2% and 20% v/v fetal calf serum, between 2.5% and 10% v/v glycerol, between 50 mM and 2 M sodium chloride, between 10 mM and 15 mM EDTA, between 0.05% and 0.1% v/v polyoxyethylene sorbitan monolaurate, 0.01% w/v trimethyltetradecylammonium bromide, and 0.5% w/v gentamycin sulfate at a final pH of 7.5 to 8.5.

12. An aqueous reagent composition for stabilizing therein an antigen or a polypeptide comprising:

a buffer, a serum, glycerol, a salt selected from the group consisting of potassium chloride, sodium chloride, magnesium chloride, magnesium sulfate, and calcium chloride, a chelating agent selected from the group consisting of EGTA and EDTA, a detergent selected from the group consisting of CHAPS, cholic acid, deoxycholic acid, digitonin, n-dodecyl-β-D-maltoside, glycodeoxycholic acid, n-lauroylsarcosine, lauryl sulfate, saponin, polyoxyethylene sorbitan monooleate, and polyethylene glycol P-1,1,3,3-tetramethylbutylphenyl ether and a preservative at a final pH of 7.5 to 8.5, wherein said composition does not comprise N-dodecanoyl-N-methylglycine or decanoyl N-methylgluconamide.

13. The aqueous reagent of claim 12, wherein said serum is fetal calf serum.

14. The aqueous reagent of claim 12 further comprising said antigen or polypeptide.

15. The aqueous reagent of claim 14 wherein the antigen or polypeptide is derived from a microorganism.

16. The aqueous reagent of claim 15, wherein said microorganism is a virus.

17. The aqueous reagent of claim 15, wherein said microorganism is a bacteria.

18. The aqueous reagent of claim 16, wherein said virus is influenza.

19. The aqueous reagent of claim 18, wherein said influenza is influenza B.

20. The aqueous reagent of claim 14, wherein said antigen is a nucleoprotein.

* * * * *